(12) United States Patent
Cerutti et al.

(10) Patent No.: US 9,689,784 B2
(45) Date of Patent: Jun. 27, 2017

(54) DEVICE AND METHOD OF CHARACTERIZATION OF THE ELASTIC PROPERTIES OF A FRICTION MATERIAL

(71) Applicant: Freni Brembo S.p.A., Curno, Bergamo (IT)

(72) Inventors: Andrea Cerutti, Curno (IT); Cristian Malmassari, Curno (IT); Pietro Barale, Curno (IT); Francesco Cucchi, Curno (IT); Massimo Torda, Curno (IT)

(73) Assignee: Freni Brembo S.p.A., Curno (IT)

( * ) Notice: Subject to any disclaimer, the term of this patent is extended or adjusted under 35 U.S.C. 154(b) by 0 days.

(21) Appl. No.: 15/027,641

(22) PCT Filed: Oct. 9, 2014

(86) PCT No.: PCT/IB2014/065167
§ 371 (c)(1),
(2) Date: Apr. 6, 2016

(87) PCT Pub. No.: WO2015/052670
PCT Pub. Date: Apr. 16, 2015

(65) Prior Publication Data
US 2016/0245733 A1   Aug. 25, 2016

(30) Foreign Application Priority Data

Oct. 9, 2013  (IT) .............................. MI2013A1669

(51) Int. Cl.
*G01N 3/38* (2006.01)
(52) U.S. Cl.
CPC ....... *G01N 3/38* (2013.01); *G01N 2203/0005* (2013.01); *G01N 2203/0019* (2013.01);
(Continued)

(58) Field of Classification Search
CPC ....................................................... G01N 3/38
(Continued)

(56) References Cited

U.S. PATENT DOCUMENTS 3,575,045 A * 4/1971 Knights .................. G01N 3/36
73/797
3,699,808 A  10/1972 Ford et al.
(Continued)

FOREIGN PATENT DOCUMENTS

JP   2005-249612 A   9/2005

*Primary Examiner* — Lisa Caputo
*Assistant Examiner* — Octavia Hollington
(74) *Attorney, Agent, or Firm* — Blank Rome LLP

(57) ABSTRACT

A device (100) of characterization of the elastic properties of a friction material, comprising: —a support yoke (1) having a body (2) with a monoblock structure surrounding an inner chamber (3); —said inner chamber (3) being defined superiorly by a first monoblock body portion (2) or upper crossbar (4); —said inner chamber (3) being defined inferiorly by a second monoblock body portion (2) or lower crossbar (5); —said upper (4) and lower (5) crossbars being mutually connected by two side columns (6, 7) formed by a third and a fourth monoblock body portions (2); —said monoblock body comprising at least one access opening (8) to the inner chamber (3); —said upper crossbar comprising a threaded through hole (9) defining a device axis (X-X) arranged substantially orthogonal to said upper crossbar (4) and said lower crossbar (5) fully passing through the inner chamber (3); —said support yoke <(1) houses, substantially completely in said inner chamber (3), a measuring column (10); said measuring column (10) comprising transmission components of a static and dynamic actions, said components being arranged not necessarily in the order indicated herein below and being mutually arranged stacked substantially along said device axis (X-X) and suitable to be packed (Continued)

together between said upper (4) and lower (5) crossbars so as to transmit a static or dynamic action from one and the other: a preloading screw (11) suitable to engage in said threaded through hole (9) with at least one threaded length (22) thereof to enter said inner chamber (3) according to a predetermined displacement with respect to said upper crossbar (4) along substantially said device axis (X-X) to exert, once the measuring column (10) has been packed, a predetermined static preloading action; an actuator (12) capable of exerting, substantially along said device axis (X-X) an oscillatory thrust action having a predetermined period that is also variable in time in a controlled manner; —at least one load cell—(13) suitable to detect the preloading action and the oscillatory thrust action exerted by said actuator; at least one specimen support portion (14) to support a specimen of material to be tested (15) suitable to receive the preloading action by the preloading screw (11) and/or the oscillatory action of the actuator (12) and to transmit it to the specimen of material to be tested (15); at least one acceleration sensor or accelerometer (16) connected to said at least one support portion (14) to detect at least the acceleration of the support portion (14) generated by said oscillatory thrust action of the actuator (12); wherein—said measuring column (10) comprises a centering shaft (18). coupled to the end (17) of said preloading screw (11) projecting into said inner chamber (3); said centering shaft having a geometry substantially with a symmetry plane parallel to the device axis (X-X); said centering shaft (18) comprises at least one pair of geometric coupling portions (19) mutually arranged in opposite positions and for the direct or indirect geometric coupling to the monoblock body (2) of the support yoke (1), so as to be coupled to said centering screw to receive therefrom the axial preloading thrust but to avoid transmitting torsion actions to the remaining part of the measuring column (10), so as to transmit to said actuator (12) substantially a direct preloading action substantially along said device axis (X-X);

—said measuring column (10) further comprises at least a ball joint (42) suitable to compensate for possible thrust misalignments between said preloading screw (11) and said actuator (12), and/or between said actuator (12) and said specimen support portion (14).

10 Claims, 7 Drawing Sheets

(52) U.S. Cl.
CPC ............... *G01N 2203/0051* (2013.01); *G01N 2203/0075* (2013.01); *G01N 2203/0094* (2013.01); *G01N 2203/0252* (2013.01); *G01N 2203/0676* (2013.01)

(58) Field of Classification Search
USPC .......................................................... 73/811
See application file for complete search history.

(56) References Cited

U.S. PATENT DOCUMENTS

| | | | | |
|---|---|---|---|---|
| 4,445,381 | A | 5/1984 | Russenberger | |
| 4,869,112 | A * | 9/1989 | Gram | G01N 3/08 73/796 |
| 5,095,757 | A * | 3/1992 | Larsen | G01N 3/04 73/857 |
| 5,425,276 | A | 6/1995 | Gram et al. | |
| 6,813,960 | B1 * | 11/2004 | Owen | G01N 3/32 73/794 |
| 7,543,506 | B2 * | 6/2009 | Merendino, Sr. | G01N 3/38 73/777 |
| 7,568,397 | B2 * | 8/2009 | Merendino, Sr. | G01N 3/04 73/818 |
| 8,528,415 | B2 * | 9/2013 | McKnight | G01N 3/08 73/818 |

* cited by examiner

DEVICE AND METHOD OF CHARACTERIZATION OF THE ELASTIC PROPERTIES OF A FRICTION MATERIAL

SPHERE OF THE INVENTION

The present invention relates to elastic properties of a friction material characterization device and a method.

In particular, the present invention relates to a device and a method for the characterization of static and dynamic elastic properties of a friction material, such as a friction material for brake pads of a braking system.

For example, during the development of a braking system, in order to identify the comfort issues of the system, specific analysis of the finished elements is conducted, using a numerical model, for example linear, which calculates the stability of the entire vehicle suspension. For this calculation to be accurate, the elastic properties of the materials involved need to be correctly defined, a definition that is complex, especially for friction material, which exhibits behaviour highly dependent on the frequencies of the stresses and loads, imposed (non-linearity of the material).

A good definition of the characteristics of the material in all conditions has the immediate advantage of achieving numerical results increasingly in accord with experimental results given for example by dynamic benches and road tests, reducing the implementation time of a solution and the reliability thereof.

STATE OF THE ART

Instruments are known of for the frequency characterization of elastic constants of friction materials but have considerable limitations due to the strong influence of the measuring chain, in particular of the structure of the measuring device which limits the actions applicable even at limited frequencies, since the deformation and vibration modes of the structure of the measuring device come to overlap the response detected of the material being analysed.

For example, solutions are known from KR20030075496A, U.S. Pat. No. 7,398,669B2.

None of these known solutions suggests how to limit the influence of the test device structure or measuring device on measurements of the static and dynamic response of the specimen concerned.

SOLUTION

Consequently the purpose of the present invention is to propose a device and a method for the characterization of the elastic properties of a friction material which makes it possible to overcome the drawbacks of the state of the art.

A further purpose of the present invention is to provide a device for the characterization of a friction material which is simple to construct but above all reliable in its measurements, reducing the influence of the deformation and static and dynamic stretch of the device structure itself.

A further purpose of the present invention is to provide a device for the characterization of a friction material which reduces the influence of the excitation component.

DRAWINGS

Further characteristics and advantages of the device according to the invention will, in any case, be evident from the description given below of its preferred embodiments, made by way of a non-limiting example with reference to the appended drawings, wherein.

DESCRIPTION OF SOME PREFERRED EMBODIMENTS

Figure 1:
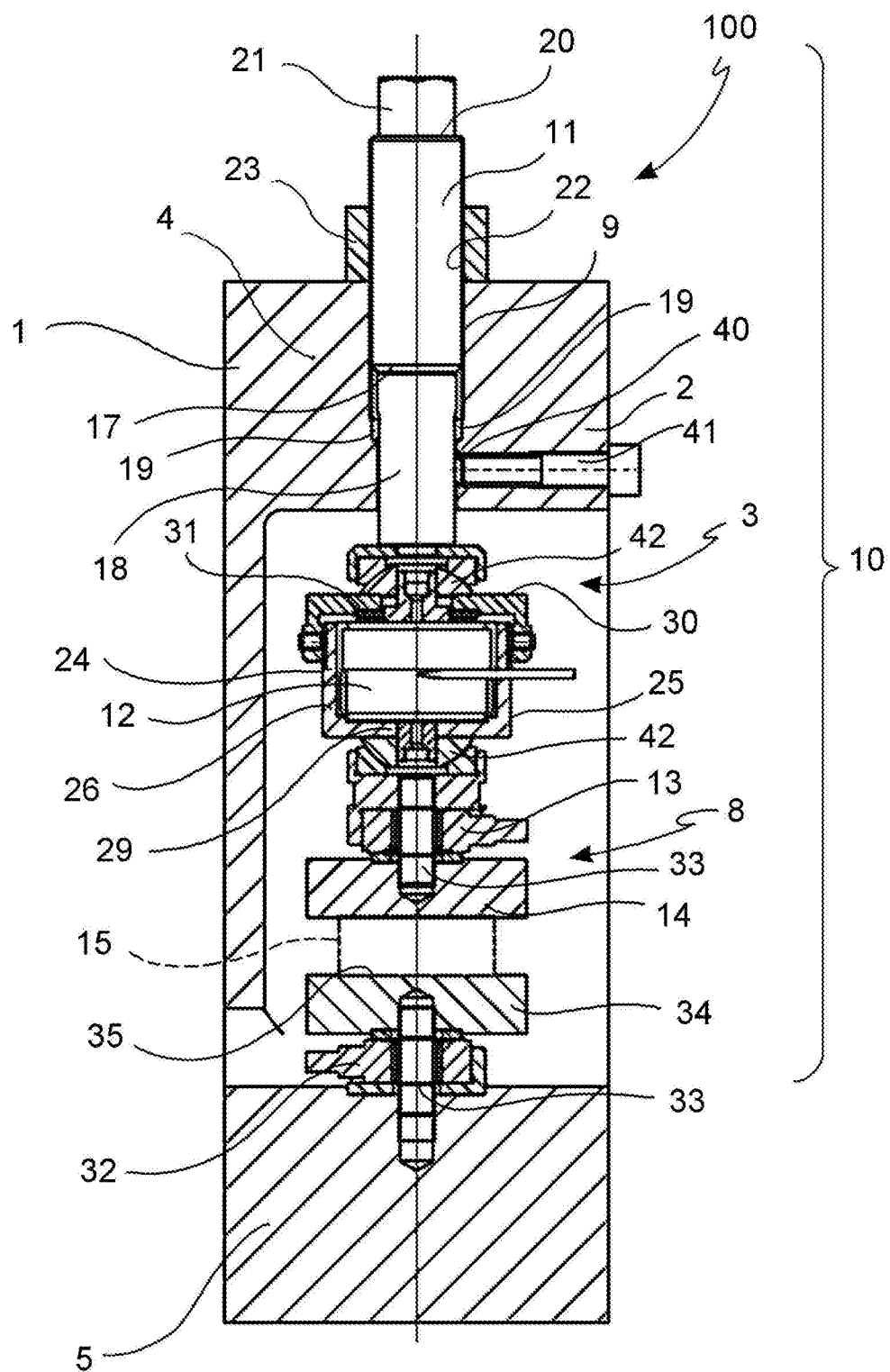
FIG. 1 shows in a transversal cross-section along the axis of the device (X-X), a device of characterization of the elastic properties of a friction material.
Figure 2:
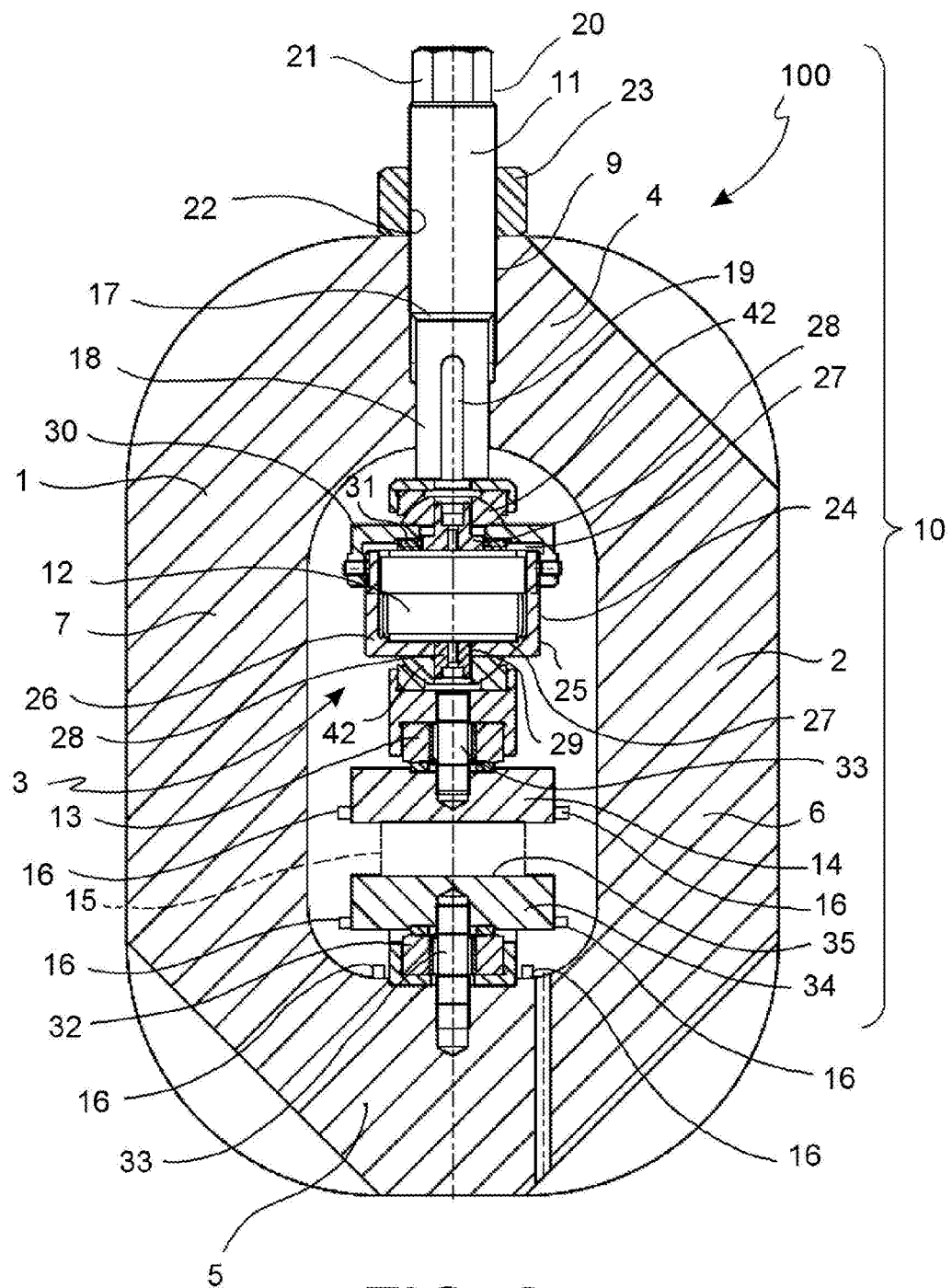
FIG. 2 shows in a front cross-section along the axis of the device (X-X), a device of characterization of the elastic properties of a friction material in FIG. 1.
Figure 3:
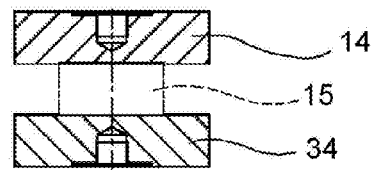
FIG. 3 shows in a transversal cross-section along the axis of the device (X-X) a pair of specimen support portions or support plates which pack-close a specimen of material to be tested.
Figure 4:
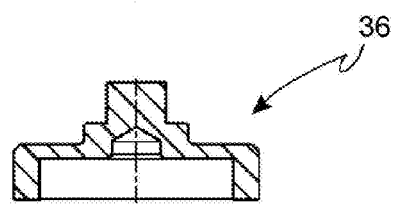
FIG. 4 shows in a transversal cross-section along the axis of the device (X-X), a manoeuvring wrench for the assembly and dismantling of the support plates.
Figure 5:
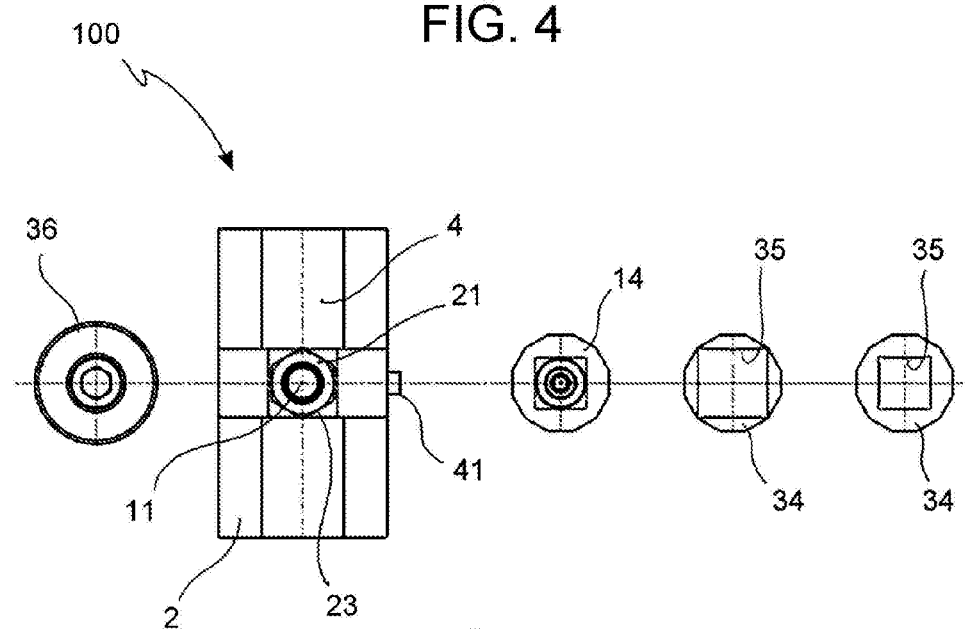
FIG. 5 shows in a view from above a device according to FIG. 1, alongside a manoeuvring wrench for assembling and dismantling the support plates and a pair of support plates which pack-close a specimen of material to be tested, as well as two other small plates with specimen seats of different sizes.
Figure 6:
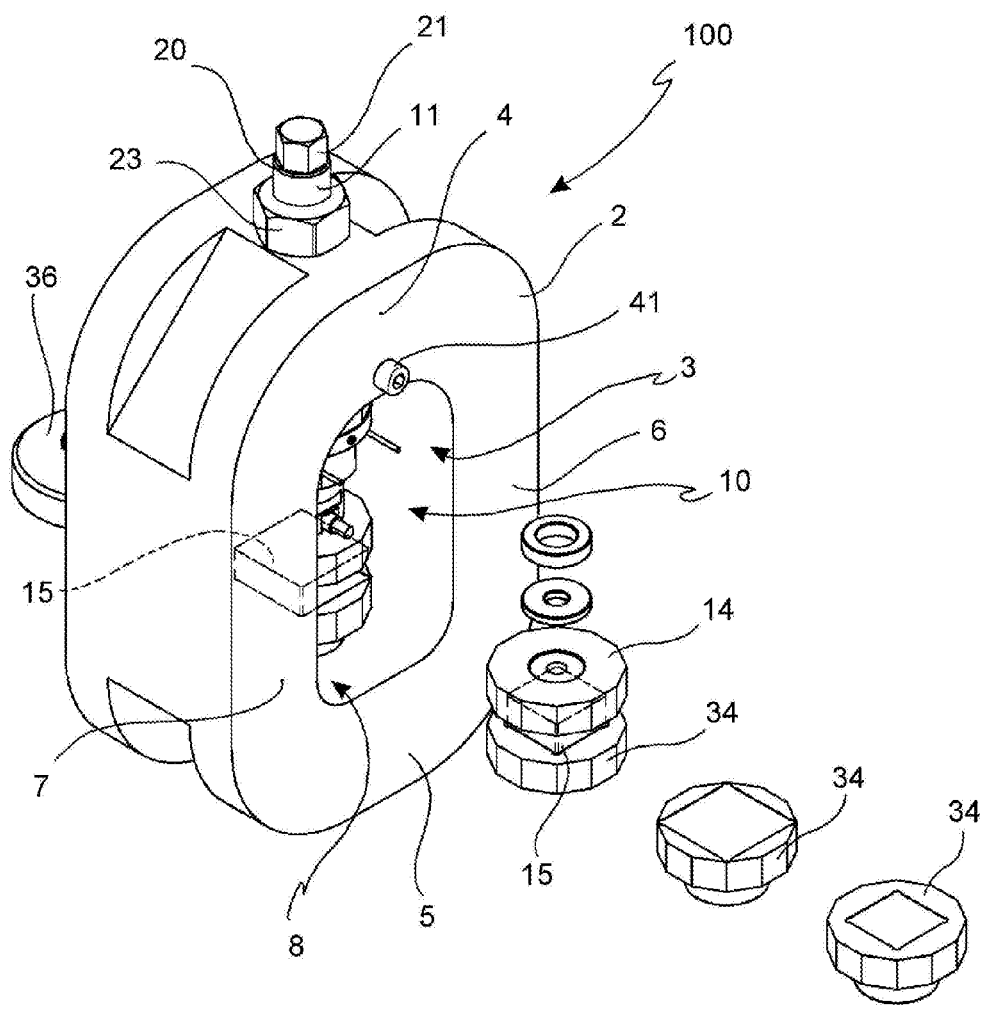
FIG. 6 shows in an axonometric view the assembly in FIG. 5.
Figure 7:
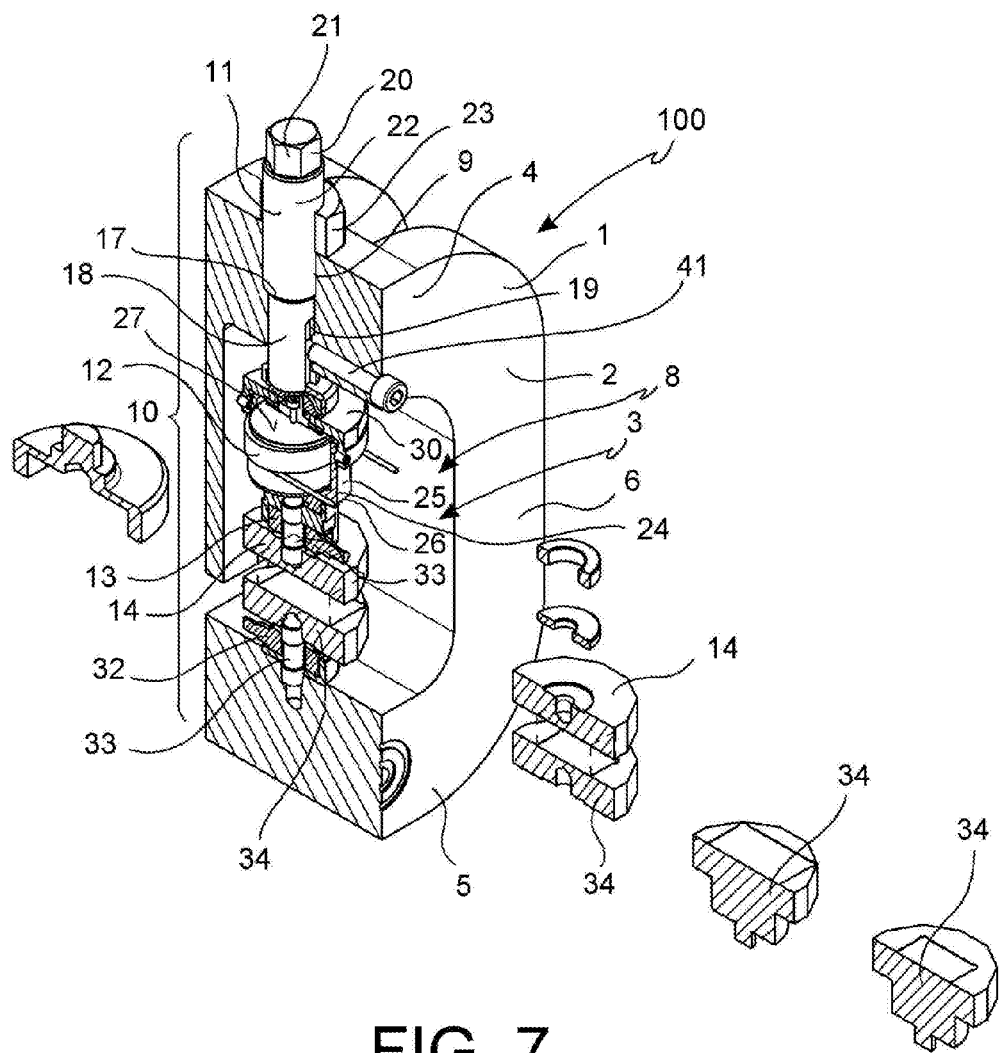
FIG. 7 shows in an axonometric view sectioned along an axis of the device (X-X) the assembly in FIG. 5.
Figure 8:
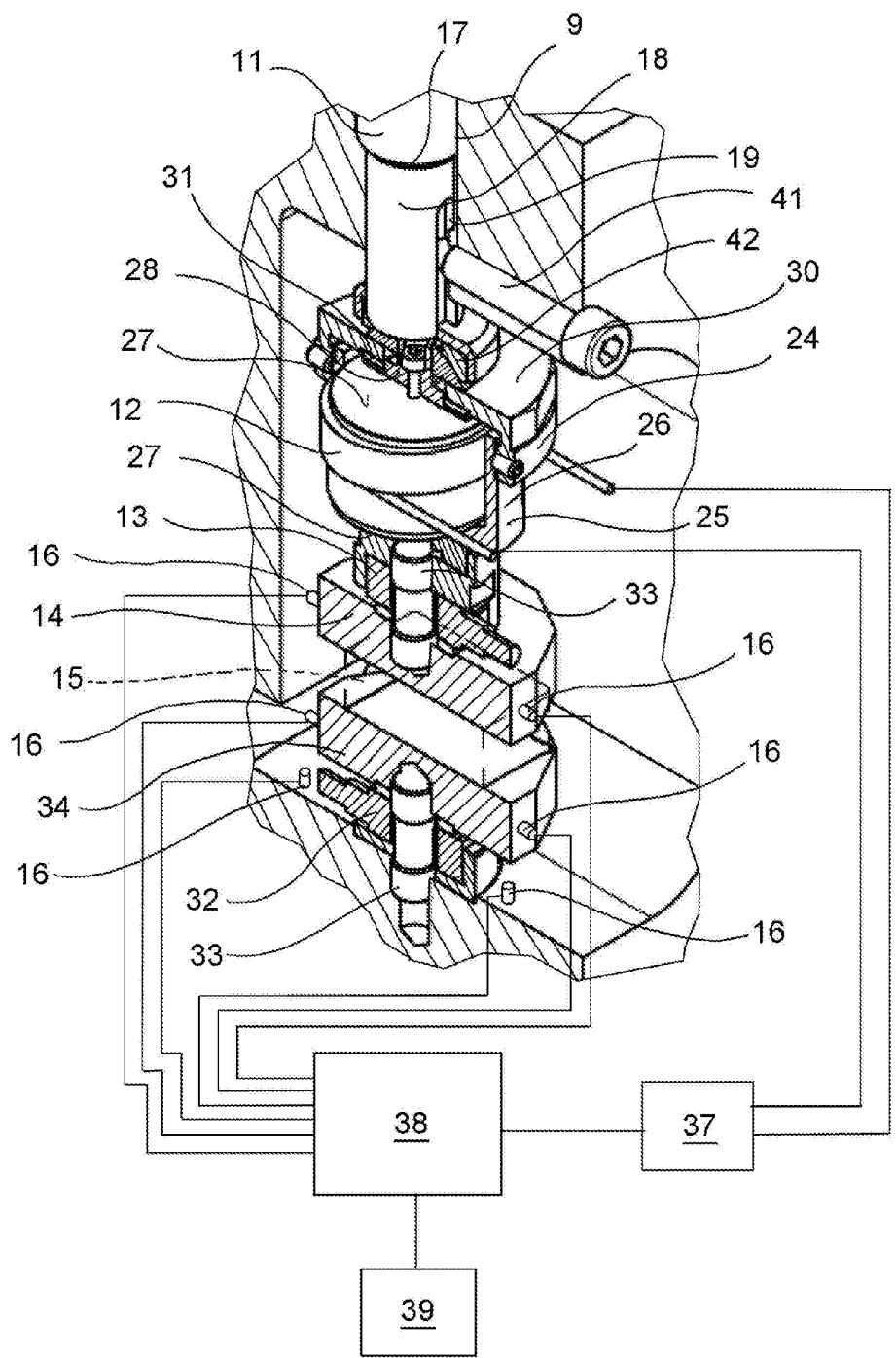
FIG. 8 shows a detail of FIG. 7.
Figure 9:
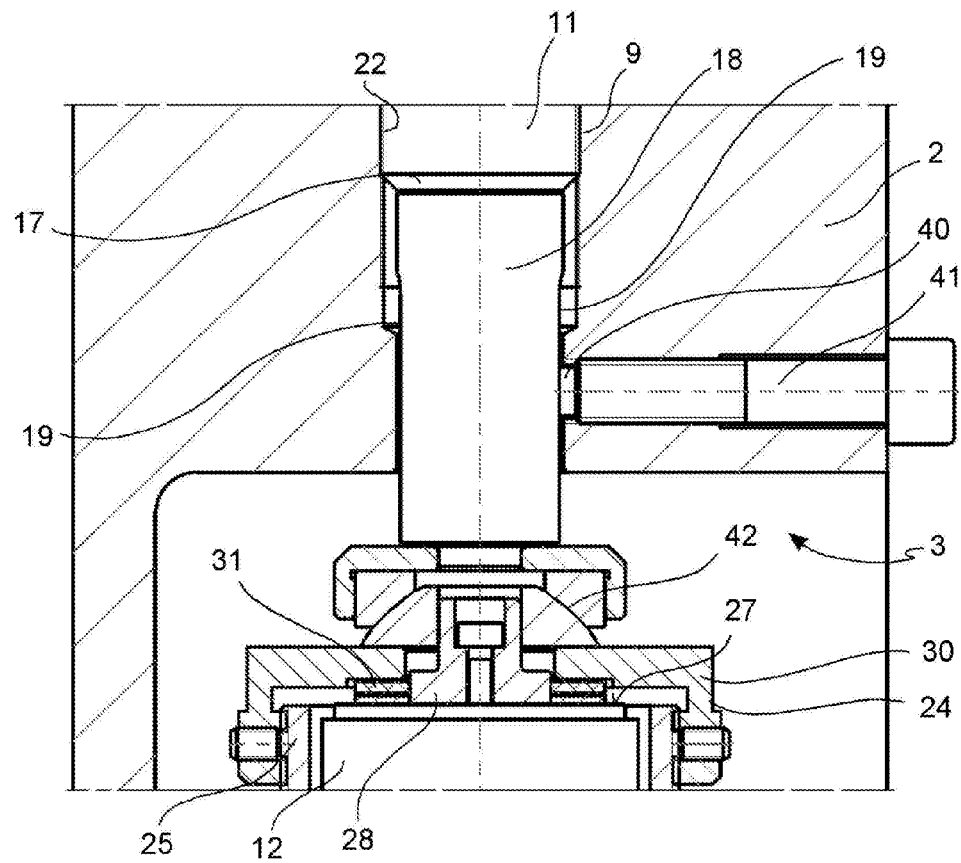
FIG. 9 shows a detail of FIG. 1 in which the centering shaft, the ball joint and the axial bearing of the preloading case of the actuator are highlighted.
Figure 10:
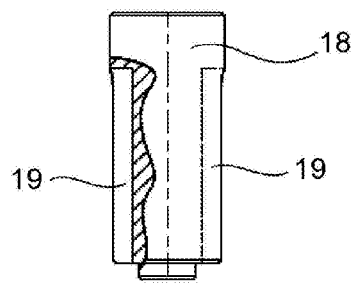
FIGS. 10 and 11 show a centering shaft also partially in cross-section.
Figure 11:
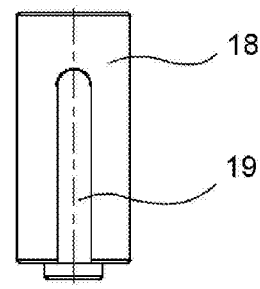

With reference to the above figures, a device of characterization 100 of the elastic properties of friction material, comprises a support yoke 1 having a body 2 with a monoblock, or in a single piece, structure surrounding an inner chamber 3.

Said inner chamber 3 is defined at the top by a first monoblock body portion 2 or upper crossbar 4, and below by a second monoblock body portion 2 or lower crossbar 5.

Said upper 4 and lower 5 crossbars are mutually connected by two side columns 6, 7 formed by a third and a fourth monoblock body portion 2 so as to close said inner chamber 3 in the manner of a monoblock ring or yoke.

Said monoblock body comprises at least one access opening 8 to the inner chamber 3.

Said upper crossbar 4 comprises a through hole 9, preferably threaded, which defines a device axis X-X arranged substantially orthogonal to said upper crossbar 4 and said lower crossbar 5 so as to pass fully through the inner chamber 3.

Said support yoke 1 houses, substantially completely in said inner chamber 3, a measuring column 10.

Said measuring column 10 comprises transmission components of a static and dynamic action to a specimen of material to be analysed or tested. said components are arranged not necessarily in the order indicated herein below and are mutually arranged stacked or in series substantially along said device axis (X-X), resulting inserted between said upper crossbar 4 and said lower crossbar 5 so as to be suitable to rest one on the other or be packed between said upper 4 and lower 5 crossbars so as to transmit a static or dynamic action from one to the other.

According to one embodiment, said measuring column comprises a preloading screw 11 suitable to engage in said threaded through hole 9 with at least one threaded length 22 thereof to enter said inner chamber 3 at least partially and perform a predetermined displacement with respect to said upper crossbar 4 substantially along said device axis X-X to exert, once the measuring column 10 has been packed, a predetermined static preloading action on said column when in operating conditions with the specimen 15 to be tested in place.

According to one embodiment, said measuring column 10 comprises an actuator 12 capable of exerting, substantially along said device axis X-X an oscillatory thrust action having a predetermined period that is also variable in time in a controlled manner.

According to one embodiment, said measuring column 10 comprises at least one load cell 13 suitable to detect the preloading action and the oscillatory thrust action exerted by said actuator.

According to one embodiment, said measuring column comprises at least one specimen support portion 14 to support a specimen of material to be tested 15 and suitable to receive the preloading action by the preloading screw 11 and/or the oscillatory action of the actuator 12 and to transmit it to the specimen of material to be tested 15.

According to one embodiment, said measuring column 10 comprises at least one acceleration sensor or accelerometer 16 connected to said at least one support portion 14 to detect at least the acceleration of the support portion 14 generated by said oscillatory thrust action of the actuator 12 overlapping said preload.

According to one embodiment, said measuring column 10 comprises a centering shaft 18 coupled to the end 17 of said preloading screw 11 projecting into said inner chamber 3.

According to one embodiment, said centering shaft has a geometry substantially with a symmetry plane parallel to the device axis X-X.

According to one embodiment, said centering shaft 18 comprises at least one pair of geometric coupling portions 19 mutually arranged in opposite positions and for the direct or indirect geometric coupling to the monoblock body 2 of the support yoke 1, so as to be coupled to said centering screw to receive therefrom the axial preloading thrust, but to avoid transmitting torsion actions to the rest of the measuring column 10, so as to substantially transmit to said actuator 12 a preloading action directed substantially according to said device axis X-X.

According to one embodiment, said measuring column further comprises at least a ball joint 42 suitable to compensate for possible thrust misalignments between said preloading screw 11 and said actuator 12, and/or between said actuator 12 and said specimen support portion 14.

According to one embodiment, said preloading screw 11 comprises a maneuver portion 20 going out outwardly of the monoblock body 2 of the support yoke 1 and has grip members 21 for gripping and maneuvering said preloading screw 11 to rotate and bring said preloading screw 11 to the desired position relative to said upper crossbar 4.

According to one embodiment, said grip members 21 are, for example, a faceted wrench portion for coupling with a maneuvering wrench or a tool.

According to one embodiment, said maneuvering or manover portion comprises a portion of said threaded length 22 of the preloading screw 11, said portion of said threaded length 22 projecting outwardly from said monoblock body 2 and being coupled with a clamping nut 23 for clamping the preloading screw at the desired position.

According to one embodiment, the measuring column components that transmit the static preloading action imposed by the preloading screw 11 and/or the oscillatory action imposed by the actuator 12 have a symmetry plane parallel to the device axis X-X so as to reduce non-symmetric deformations and/or to increase the frequency of the intrinsic vibrational modes of these components.

According to one embodiment, said preloading screw 11 is a screw with a micrometric threaded length 22 to exert extremely accurate preloads.

According to one embodiment, said actuator 12 is a piezoelectric actuator that may be driven in a controllable manner.

According to one embodiment, said actuator 12 has a thrust axis that is arranged substantially aligned with the device axis (X-X).

According to one embodiment, said actuator 12 has thrust surfaces 27 associated to connection and thrust means 28.

According to one embodiment, said actuator 12 is received within a preloading case 24 for preloading the actuator along its thrust axis X-X.

According to one embodiment, said actuator preloading case 24 comprises a threaded container 25 having a glass-shaped body 26 suitable to receive said actuator so as to bring an actuating end thereof to face an opening 29 so that a portion of said connection and thrust means 28 exits from said threaded container.

According to one embodiment, said actuator preloading case 24 comprises a threaded lid 30 screwed to said threaded container 25 to embed and preload said actuator received in said threaded container 25.

According to one embodiment, between said threaded lid 30 and said actuator 12 an axial bearing 31 is sandwiched, avoiding transferring the screwing torsion actions of the threaded lid 30 on the threaded container 25 to the actuator 12 so that the actuator 12 receives a substantially preloading action directed according to the actuator thrust axis from the preloading case 24.

According to one embodiment, between said threaded lid 31 and said threaded container 25 at least one pair of locking dowels 32 is provided for, which are arranged at diametrically opposite positions to keep the symmetry plane parallel to the device axis X-X of the actuator 12 and of the preloading case 24.

According to one embodiment, said measuring column 10 comprises two loading cells 13, 32 so arranged as to be located before and after, or just before and immediately after, along the device axis X-X of said measuring column 10, the specimen support portion(s) 14, 34, preferably rigidly connected thereby, in order to detect the action transmitted to the specimen support portions 14, 34, to the specimen of material to be tested 15.

According to one embodiment, said loading cells 13, 32 are rigidly connected to said support portions 14, 34 by means of threaded dowels or studs 33 received in threaded seats that are provided for in the loading cells 13 and support portions 14, 34.

According to one embodiment, a second loading cell 32 is arranged between a second specimen support portion 34 and the lower crossbar 5 and said loading cell 32 and rigidly connected to said lower crossbar 5 so as to discharge or transmit the preload exerted by the preloading screw 11 and the oscillation exerted by the actuator 12 to said monoblock body 2 closing the measuring column 10 in the monoblock body 2;

According to one embodiment, said specimen support portion 14 and said second specimen support portion 34, under operative conditions, clamp on opposite sides or pack said specimen of material to be tested 15 allowing the preloading of the measuring column 10.

According to one embodiment, said specimen support portion(s) 14, 34 comprise a resting plate forming a specimen seat 35, said resting plate having a symmetry plane parallel to the device axis X-X, for example with a section transversal to said device axis that is dodecahedral for the coupling to a dodecahedral maneuvering wrench 36 for assembling and disassembling said resting plate in the measuring column 10.

According to one embodiment, said resting plate 14, 34 comprises, centrally on its face opposite said specimen seat 35, a threaded hole for securing a dowel or stud (33) for securing the loading cell 13 to the small plate.

According to one embodiment, said at least one accelerometer 16 is a piezoelectric or capacitive accelerometer.

According to one embodiment, said at least one accelerometer 16 is at least two accelerometers mutually arranged at opposite positions of the static and oscillatory action transmission component, for example, a specimen support portion 14, 34 or resting plate.

According to one embodiment, there are provided for at least two accelerometers 16, which are connected in opposite positions to the specimen support portion 14, and two further accelerometers 16 connected in opposite positions to the second specimen support portion 34 so as to keep, for the assembly of support portion and pair of accelerometers, a symmetry plane parallel to the device axis X-X.

According to one embodiment, further accelerometers 16 connected to the lower crossbar 5 in the proximity of the connection point of the measuring column 10 or measuring column base are provided for.

According to one embodiment, a measuring chain is comprised comprising at least one drive actuator 37 for the command in a controlled manner for example in frequency, of said actuator 12.

According to one embodiment, said measuring chain comprises a signal acquisition device 38 for feeding, receiving the signal, possible digitalization of the signal, filtering of the signal and analysis of the signal in time and/or frequency of a signal from the load cell (s) 13, 32 and accelerometer (s) 16.

According to one embodiment, said measuring chain comprises a calculation device 39 of the dynamic elasticity and dynamic damping of the specimen subjected to the predetermined preload.

According to one embodiment, said centering shaft 18 comprises at least two mutually opposite grooves 19 so as to create a symmetry plane parallel to the device axis X-X, at least one of said grooves 19, under operative conditions, selectively receives a tip 40 of a stop screw 41 connected to said monoblock body 2 of the yoke 1 suitable to prevent said centering shaft 18 from rotating during the displacement of the preloading screw 11 to avoid transmitting actions different from the preload directed substantially according to the device axis X-X to the measuring column 10 components.

According to one embodiment, said measuring column 10 further comprises at least two ball joints 19 suitable to compensate for possible thrust misalignments between said preloading screw 11 and said actuator 12 and said actuator 12 and said specimen support portion 14 or said load cell 13.

According to one embodiment, said ball joint 42 is a lubricated ball joint and/or having ball joint components made of or coated with an anti- or low-friction material, e.g., Teflon®.

A method of characterization of the elastic properties of a friction material using a device of the present invention will be briefly described below.

According to one possible use, a method of characterization of the elastic properties of a friction material comprises the steps of:
applying a preload to the specimen of material to be tested 15;
applying a period- and width-controlled overlapped oscillation;
preventing the measuring column 10 from flexing by verifying the symmetry of the components transmitting said preload and said overlapped oscillation in a plane parallel to the device axis X-X;
avoiding torsion actions on said specimen 15;
correcting preload thrust and/or oscillation misalignments directed according to directions that are not coincident with or parallel to the device axis X-X.

According to one possible use, a step is provided for:
applying a preload to the specimen of material to be tested 15 so that the applied overlapped oscillation is applied about a predetermined preload value.

According to one possible use, a step is provided for detecting the applied static preload and dynamic oscillation load.

According to one possible use, a step is provided for detecting the acceleration of the specimen 15 support portion or resting plate 14, 34.

According to one possible use, a step is provided for assessing, taking into account the applied load and the acceleration response, the specimen 15 elasticity and/or dynamic damping.

Obviously, a person skilled in the art may make numerous modifications and variations to the device according to the invention so as to satisfy contingent and specific requirements while remaining within the sphere of protection of the invention as defined by the following claims.

According to one embodiment, a device 100 consists of a monoblock structure 2 (from here on called the support block) which acts as a base and rigid support for the actual measurement apparatus (measuring column 10). The required functions of the system (in the column) are: a preload, a high-frequency sinusoidal dynamic stress, the measurement of the forces acting on the specimen and the measurement of the related displacements. The active components are a screw 11 which imposes a constant force from above, a piezoelectric actuator 12 imposing frequency shifts, one or two load cells, 13, 32 and up to six accelerometers 16. Plates 14, 34 are then provided for the positioning of the specimen (and the support of the accelerometers 16), structures for the centering and preloading of the actuator and cells, ball joints 19 between the various components and the shaft for centering everything.

The measuring column is the part of the apparatus where the material to be tested is preloaded, stressed (a high-frequency sinusoidal dynamic stress) and measured (forces and displacements).

The name "column" is suggested by the packed position of each component positioned so as to rest on the next and the shape thereof which, when not having perfect axial symmetry, possesses at least one plane of symmetry parallel to the direction of forcing. The order of arrangement proposed in the following description is merely an example of assembly. The only constraint to the order is given by the functioning criteria of the elements: in particular, each load cell must have one side resting on a support plate 14, 34 (the forces acting on the specimen to be tested are measured on these), while the actuator, for example piezoelectric, can command a plate 13, 34, either of the two, on condition that a load cell is placed on this which will thus be between the two elements.

Given that the vibrational analysis involves high oscillation frequencies and displacements in the order of micrometers, the decision to maintain as much as possible a high elastic constant and axial symmetry is due to the desire to minimize any imbalance of geometries and masses which, by unbalancing the column, would result in the production of movements during functioning having a different direction from that of the column axis. In particular, the micrometric preloading screw 11 makes it possible, thanks to the fine pitch of the thread, to accurately set a pressure on the rest of the column (and thus on the specimen). A clamping nut 23 is provided.

The centering shaft 18 moves the load imposed by the screw 11 in the axial direction. The shaft 18 has a groove 19 to house the tip of a screw 41 mounted in a radial position which, once inserted from the outside, blocks the rotation of the shaft 18, offering a reaction to the torque transferred from the preloading screw 11. The shaft 18 has a second channel 19 diametrically opposite, provided to improve the symmetry of the piece in order to avoid imbalances and therefore movements in a radial direction. Again with the aim of improving the alignment of all the components, at the end of the shaft a pin for attachment with the next element may be introduced.

The lubricated spherical joint 42, for example, composed of a perforated hemispherical cap and a coupled ring nut, can be inserted between two components, permitting, during the closure of the column 10 with the application of the static load, a small relative rotation useful to improve the vertical alignment of the two elements in contact. To favour sliding, the joints, for example in steel, require lubrication (the Teflon®-coated solution which possibly overcomes this requirement may also be provided for).

The piezoelectric actuator 12 with preloading case 24 is the component which produces the high frequency dynamic stress. Controlled by a sinusoidal electric signal at a high frequency, it is capable of generating forces and displacements in the axial direction in the order of magnitude of interest following the wave function transmitted to it with a speed of response in the order of microseconds.

Since for a better functioning it is preferable to preload the component in the axial direction, use of the actuator 12 inside a preloading case 24 may be provided for.

The preloading case 24, with holes for the passage of the actuator cables 12, consists of a threaded container 25 and lid 30. The purpose of this device is to impose on the actuator, by tightening the cover 30, an axial preloading force. Between the cover 30 and the actuator 12 an axial roller bearing 31 is positioned with suitable housing seat, so that the torque imposed on the cover does not apply a torsion to the surface of the actuator, but the load is imposed only in the axial direction.

The load cell 13, 32 has the dual purpose of measuring dynamic forces related to the displacement ordered by the actuator 12 and to measure the static forces imposed by the preloading screw 11. The type of cell must therefore be able to perform both high-frequency and static measurements.

To keep all the components centred, the cell can be placed inside special steel supports. These cells may be preloaded using a stud-bolt 33, achieving a compression force regulated by the screw threads, guaranteeing an improved functioning of the device.

The support plates 14, 34 are the part of the structure which contains the specimen 15. On the surface of these components the accelerometers 16 are placed for measuring the kinematic parameters of interest.

The steel which they are preferably made of is much stiffer than the friction material of the specimen 15 and the thickness thereof is sufficient to displace the forces needed to deform them at much higher values than those generated during the functioning of the system. For this reason, the pressure they transfer is substantially uniform on the surface of the specimen and their motion is integral with its deformation. With these assumptions, the choice to place the accelerometers on them is justified, considering the displacements of the support surfaces equal to those imposed on the test material.

The faces of the support plates 14, 34 opposite the contact faces with the specimen are used for connection with the load cell, by one end of the preloading screw of the cell, or with the support block.

The support plates also have a shape which ensures a high degree of axial symmetry relative to the direction of forcing, for example with a dodecahedral section, having a high symmetry but with wrench surfaces for a manoeuvring wrench 36.

If on the one hand a circular base maximizes axial symmetry, on the other the need to tighten one of the plates to the base may justify the use of a polygon shape allowing the plate to be inserted in an adapter making it possible to move the plate by means of a wrench from the outside of the structure.

On the faces of the plate in contact with the specimen, seats 35 may be made to facilitate the centring of the specimen.

The specimen 15 is positioned between the two plates 14, 34, and may have a square or circular base. The specimen may be cut in different sizes, chosen in order to separate as far as possible the result of measurement from the effects of the heterogeneity of the material.

The measuring device proposed here allows the direct measurement of elastic constants of non-linear materials such as, in particular, friction material. In addition, the system is provided with geometry and structural rigidity such as to allow the measurement of specimens with size features in the order of centimeters, so as to minimize the influence of highly uneven local conditions of the material (metal inclusions, dust agglomerates etc.).

The device is able to provide direct information on the elastic characteristics of friction material at the precise range of frequencies involved in the whistling phenomena which are one of the main problems in the automobile industry.

The device could be used for reproducing the piston pressure which acts as static load on the pad of a braking system, such as a brake for a disc brake of a vehicle, and a high-frequency sinusoidal forcing, to reproduce the vibration imposed by the oscillation of the disc on the material.

This particular State of stress imposed on the material can be shown using the Kelvin-Voigt model for viscoelastic materials.

The behaviour of the specimen, which will be positioned and forced by two rigid surfaces, support plates 14, 34, connected to the rest of the device, is comparable to a system composed of an elastic spring and damper in parallel.

The values measured during the tests are the static and dynamic force $F_{stat}$ and $F_{din}$ (direct measurement using a load cell) and the displacements of the surface of the plate in contact with the generator of the dynamic force and the specimen base opposite the stressed plate (measure derived from accelerometers by integrating the signal twice).

Once known the forces and displacements, the characteristic magnitudes of the material are calculated In particular, to study the dynamics of the system, it is useful to consider the equilibrium equation associated with one of the two plates (below is a diagram of the forces acting on the lower plate, chosen as a reference).

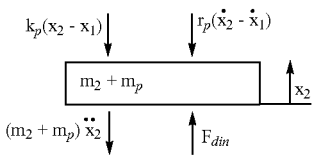

Considering the mass of the specimen incorporated in the mass of the support plate it is possible to express the dynamic equilibrium equation as:

$$(m_z+m_p)\ddot{x}_2+r_p(\dot{x}_2-\dot{x}_1)+k_p(x_2-x_1)=F_{din}$$

Where:

$(m_2+m_p)\vec{\ddot{x}}_2$ is the inertial component associated with the mass of the lower plate and the specimen;

$r_p(\dot{x}_2-\dot{x}_1)$ is the viscose dissipative component (dissipative) associated with the damping of the specimen ($r_p$);

$k_p(x_2-x_1)$ is the elastic component (conservative) associated with the stiffness of the specimen ($k_p$);

$F_{din}$ is the dynamic sinusoidal forcing imposed;

Considering a sinusoidal dynamic forcing of a known frequency, $\Omega$ it is possible to express displacements, velocities and accelerations in the following form:

$x_i = X_i e^{i\Omega t}$
$\dot{x}_i = i\Omega X_i e^{i\Omega t}$
$\ddot{x}_i = -\Omega^2 X_i e^{i\Omega t}$ The solution of the equation of motion being known, it is possible to express stiffness ($k_p$) and damping ($r_p$) of the specimen according to the Kelvin-Voigt model in the following form:

$$k_p = \text{Re}\left(\frac{F_c - (m_2 + m_p)\ddot{x}_2}{x_2 - x_1}\right)$$

$$r_p = \text{Im}\left(\frac{F_c - (m_2 + m_p)\ddot{x}_2}{\Omega(x_2 - x_1)}\right)$$

In the above formulas, the value of $F_c$ is the forcing read from the load cell, $\ddot{x}_2$ is the acceleration obtained by means of one or more accelerometers arranged on the support plate while $x_2$ and $x_1$ are the movements of the two support plates which, as said, are derived from integration of the accelerometer signals.

The results obtained are the values of stiffness and damping in the normal direction to the specimen (out-of-plane elastic modulus of the pad) at a given frequency, having imposed a specific preload. The device thus provides detailed information on the characteristics of the material in a load condition extremely similar to the state of stress to which the material is subjected during braking.

The device generates a sinusoidal forcing on the specimen. The control of this forcing, once the frequency has been selected, is operated on the magnitude of the forcing itself, the physical meaning of which is merely the displacement generated by it The information generated by the device are for example elastic modulus curves as a function of frequency, precisely one curve for each combination of preload imposed and for each forcing criterion.

REFERENCES 1 support yoke
2 monoblock body
3 monoblock body inner chamber
4 upper crossbar
5 lower crossbar
6 column
7 column
8 access opening to the inner chamber
9 threaded through hole
10 measuring column
11 preloading screw
12 actuator
13 load cell
14 specimen support portion
15 specimen of material to be tested
16 accelerometer
17 inner end of the centering screw
18 centering shaft
19 portions of geometric coupling between centering shaft and monoblock body
20 manoeuvre portion of the preloading screw
21 grip members
22 threaded length of the preloading screw
23 clamping nut
24 preloading case
25 threaded container
26 glass-shaped body
27 thrust surfaces
28 connection and thrust means
29 threaded container opening
30 threaded lid
31 axial bearing
32 second load cell
33 connection stud-bolts of the load cells
34 second specimen support portion
35 specimen seat
36 dodecahedral manoeuvring wrench
37 drive actuator
38 signal acquisition device
39 calculation device
40 tip of the centering shaft stop screw
41 stop screw
42 ball joint
100 device
X-X device axis

The invention claimed is:

1. An elastic properties of a friction material characterization device, comprising:
a support yoke having a body with a monoblock structure surrounding an inner chamber;
said inner chamber being defined superiorly by a upper crossbar, formed by a first monoblock body portion;
said inner chamber being defined inferiorly by a lower crossbar formed by a second monoblock body portion;
said upper and lower crossbars being mutually connected by two side columns formed by a third and a fourth monoblock body portions;
said monoblock body comprising at least one access opening to the inner chamber;

said upper crossbar comprising a threaded through hole defining a device axis arranged substantially orthogonal to said upper crossbar and said lower crossbar fully passing through the inner chamber;

said support yoke houses, substantially completely in said inner chamber, a measuring column;

said measuring column comprising transmission components of a static and dynamic actions, said components being arranged not necessarily in the order indicated herein below and being mutually arranged stacked substantially along said device axis and suitable to be packed together between said upper and lower crossbars so as to transmit a static or dynamic action from one and the other:

a preloading screw suitable to engage in said threaded through hole with at least one threaded length thereof to enter said inner chamber according to a predetermined displacement with respect to said upper crossbar along substantially said device axis to exert, once the measuring column has been packed, a predetermined static preloading action;

an actuator capable of exerting, substantially along said device axis an oscillatory thrust action having a predetermined period that is also variable in time in a controlled manner;

at least one load cell suitable to detect the preloading action and the oscillatory thrust action exerted by said actuator;

at least one specimen support portion to support a specimen of material to be tested suitable to receive the preloading action by the preloading screw or the oscillatory action of the actuator and to transmit it to the specimen of material to be tested;

at least one acceleration sensor or accelerometer connected to said at least one support portion to detect at least the acceleration of the support portion generated by said oscillatory thrust action of the actuator;

wherein:

said measuring column comprises a centering shaft coupled to the end of said preloading screw projecting into said inner chamber;

said centering shaft having a geometry substantially with a symmetry plane parallel to the device axis;

said centering shaft comprises at least one pair of geometric coupling portions mutually arranged in opposite positions and for the direct or indirect geometric coupling to the monoblock body of the support yoke, so as to be coupled to said preloading screw to receive therefrom the axial preloading thrust, but avoiding transmitting torsion actions to the rest of the measuring column, so as to substantially transmit a preloading action directed substantially according to said device axis to said actuator;

said measuring column further comprises at least a ball joint suitable to compensate for possible thrust misalignments between said preloading screw and said actuator, or between said actuator and said specimen support portion.

2. The device according to claim 1, wherein said preloading screw comprises a maneuver portion going out outwardly of the monoblock body of the support yoke and has grip members for gripping and maneuvering said preloading screw to rotate and bring said preloading screw to the desired position relative to said upper crossbar; or wherein said grip members are a faceted wrench portion for coupling with a maneuvering wrench or a tool; or wherein said maneuver portion comprises a portion of said threaded length of the preloading screw, said portion of said threaded length projecting outwardly from said monoblock body and being coupled with a clamping nut for clamping the preloading screw at the desired position; or wherein the measuring column components that transmit the static preloading action imposed by the preloading screw or the oscillatory action imposed by the actuator have a symmetry plane parallel to the device axis so as to reduce non-symmetric deformations or to increase the frequency of the intrinsic vibrational modes of these components; or wherein said preloading screw is a screw with a micrometric threaded length.

3. The device according to claim 1, wherein said actuator is a piezoelectric actuator that may be driven in a controllable manner; or wherein said actuator has a thrust axis that is arranged substantially aligned with the device axis; or wherein said actuator has thrust surfaces associated to connection and thrust means; or wherein said actuator is received within a preloading case for preloading the actuator along its thrust axis; or wherein said actuator preloading case comprises a threaded container having a glass-shaped body suitable to receive said actuator so as to bring an actuating end thereof to face an opening so that a portion of said connection and thrust means exits from said threaded container; or wherein said actuator preloading case comprises a threaded lid screwed to said threaded container to embed and preload said actuator received in said threaded container; or wherein, between said threaded lid and said actuator, an axial bearing is sandwiched, avoiding transferring the screwing torsion actions of the threaded lid on the threaded container to the actuator so that the actuator receives a substantially preloading action directed according to the actuator thrust axis from the preloading case; or wherein between said threaded lid and said threaded container at least one pair of locking dowels is provided for, which are arranged at diametrically opposite positions to keep the symmetry plane parallel to the device axis of the actuator and of the preloading case.

4. The device according to claim 1, wherein said measuring column comprises two loading cells, so arranged as to be located before and after, or just before and immediately after, along the device axis of said measuring column, the specimen support portion(s), preferably rigidly connected thereby, in order to detect the action transmitted to the specimen support portions, to the specimen of material to be tested; or wherein said loading cells are rigidly connected to said support portions by means of threaded dowels or studs received in threaded seats that are provided for in the loading cells and support portions; or wherein a second loading cell is arranged between a second specimen support portion and the lower crossbar and said loading cell and rigidly connected to said lower crossbar so as to discharge or transmit the preload exerted by the preloading screw and the oscillation exerted by the actuator to said monoblock body closing the measuring column in the monoblock body; or wherein said specimen support portion and said second specimen support portion, under operative conditions, clamp on opposite sides or pack said specimen of material to be tested allowing preloading the measuring column; or wherein said specimen support portion(s) comprise a resting plate forming a specimen seat, said resting plate having a symmetry plane parallel to the device axis, for example with a section transversal to said dodecahedral device axis for the coupling to a dodecahedral maneuvering wrench for assembling and disassembling said resting plate in the measuring column; or wherein said resting plate comprises, centrally on its face opposite said specimen seat, a threaded hole for securing a dowel or stud for securing the loading cell to the small plate.

5. The device according to claim 1, wherein said at least one accelerometer is a piezoelectric or capacitive accelerometer; or wherein said at least one accelerometer is at least two accelerometers arranged at opposite positions of the static and oscillatory action transmission component, for example, a specimen support portion or resting plate;

there are provided for at least two accelerometers, which are connected in opposite positions to the specimen support portion, and two further accelerometers connected in opposite positions to the second specimen support portion so as to keep, for the assembly of support portion and pair of accelerometers, a symmetry plane parallel to the device axis; or wherein further accelerometers connected to the lower crossbar in the proximity of the connection point of the measuring column or measuring column base are provided for.

6. The device according to claim 1, wherein a measuring chain is comprised, which comprises at least one operation of actuator for driving in a controlled manner, for example, a frequency controlled manner, said actuator; or wherein said measuring chain comprises a signal acquisition device for feeding, receiving, filtering the signal and time or frequency analysis of a signal from the loading cell(s) and accelerometer(s); or wherein said measuring chain comprises a device for calculating the dynamic elasticity and the dynamic damping of the specimen that is subjected to the predetermined preload.

7. The device according to claim 1, wherein said centering shaft comprises at least two mutually opposite grooves so as to create a symmetry plane parallel to the device axis, at least one of said grooves, under operative conditions, selectively receives a tip of a stop screw connected to said monoblock body of the yoke suitable to prevent said centering shaft from rotating during the displacement of the preloading screw to avoid transmitting actions different from the preload directed substantially according to the device axis to the measuring column components.

8. The device according to claim 1, wherein said measuring column further comprises at least two ball joints suitable to compensate for possible thrust misalignments between said preloading screw and said actuator, and between said actuator and said specimen support portion or said load cell; or wherein said ball joint is a lubricated ball joint or having ball joint components made of or coated with an anti- or low-friction material, e.g., Teflon®.

9. A method for the characterization of the elastic properties of a friction material by a device according to claim 1, wherein the steps are provided for, of:

applying a preload to the specimen of material to be tested;

applying a period- and width-controlled overlapped oscillation;

preventing the measuring column from flexing by verifying the symmetry of the components transmitting said preload and said overlapped oscillation in a plane parallel to the device axis;

avoiding torsion actions on said specimen;

correcting preload thrust or oscillation misalignments directed according to directions that are not coincident with or parallel to the device axis.

10. The method according to claim 9, wherein the step is provided for, of:

applying a preload to the specimen of material to be tested so that the applied overlapped oscillation is applied about a predetermined preload value; or wherein the step is provided for, of:

detecting the applied static preload and dynamic oscillation load; or wherein the step is provided for, of detecting the acceleration of the specimen support portion or resting plate; or wherein the step is provided for, of:

assessing, taking into account the applied load and the acceleration response, the specimen elasticity or dynamic damping.

* * * * *